United States Patent
Budoff

(10) Patent No.: US 8,939,984 B2
(45) Date of Patent: Jan. 27, 2015

(54) METHOD OF PERFORMING OSTEOTOMY

(75) Inventor: Jeffrey E. Budoff, Bellaire, TX (US)

(73) Assignee: TriMed, Inc., Santa Clarita, CA (US)

(*) Notice: Subject to any disclaimer, the term of this patent is extended or adjusted under 35 U.S.C. 154(b) by 143 days.

(21) Appl. No.: 13/294,648

(22) Filed: Nov. 11, 2011

(65) Prior Publication Data

US 2012/0130383 A1 May 24, 2012

Related U.S. Application Data

(60) Provisional application No. 61/414,999, filed on Nov. 18, 2010.

(51) Int. Cl.
| | | |
|---|---|---|
| *A61B 17/56* | (2006.01) | |
| *A61B 17/15* | (2006.01) | |
| *A61B 17/88* | (2006.01) | |
| *A61B 17/17* | (2006.01) | |

(52) U.S. Cl.
CPC ........... *A61B 17/152* (2013.01); *A61B 17/8866* (2013.01); *A61B 2017/1782* (2013.01)
USPC .............................................. 606/87; 606/88

(58) Field of Classification Search
CPC .... A61B 17/58; A61B 17/88; A61B 17/8866; A61B 17/15; A61B 17/151; A61B 17/152; A61B 17/17; A61B 17/1739; A61B 2017/1782
USPC ........... 606/79, 82, 86 R, 87–90, 96–98, 102, 606/104
See application file for complete search history.

(56) References Cited

U.S. PATENT DOCUMENTS

| | | | | |
|---|---|---|---|---|
| 5,449,360 | A | * | 9/1995 | Schreiber .......................... 606/87 |
| 5,540,695 | A | * | 7/1996 | Levy ................................ 606/87 |
| 5,613,969 | A | * | 3/1997 | Jenkins, Jr. ...................... 606/87 |
| 5,935,128 | A | * | 8/1999 | Carter et al. ................. 606/86 B |
| 5,980,526 | A | * | 11/1999 | Johnson et al. .............. 606/86 R |
| 7,364,581 | B2 | * | 4/2008 | Michalowicz .................. 606/87 |
| 8,241,293 | B2 | * | 8/2012 | Stone et al. ..................... 606/87 |
| 2002/0164905 | A1 | * | 11/2002 | Bryant .......................... 439/894 |
| 2005/0273114 | A1 | * | 12/2005 | Novak ............................ 606/88 |
| 2006/0079963 | A1 | * | 4/2006 | Hansen ....................... 623/19.11 |
| 2007/0233145 | A1 | * | 10/2007 | Richardson et al. ............. 606/90 |
| 2007/0265634 | A1 | * | 11/2007 | Weinstein ........................ 606/87 |
| 2008/0262500 | A1 | * | 10/2008 | Collazo ........................... 606/88 |

* cited by examiner

*Primary Examiner* — Todd Manahan
*Assistant Examiner* — Marcela I Shirsat
(74) *Attorney, Agent, or Firm* — Wood, Phillips, Katz, Clark & Mortimer

(57) ABSTRACT

A method of performing an osteotomy including the steps of: providing a guide assembly; placing the guide assembly in operative relationship to a bone to be cut so that the guide assembly defines first and second guide edges that are in fixed relationship to each other to each guide movement of a cutting tool; guiding the cutting tool along each of the first and second guide edges to produce first and second cut lines in the bone to facilitate separation of a fragment of the bone from between first and second bone surfaces formed respectively at the first and second cut lines; separating the bone fragment so that a gap with a first width is formed between the first and second bone surfaces; and changing the width of the gap to be less than the first width.

23 Claims, 10 Drawing Sheets

METHOD OF PERFORMING OSTEOTOMY

BACKGROUND OF THE INVENTION

1. Field of the Invention

This invention relates to osteotomies and, more particularly, to a method for facilitating predictable bone removal in terms of size, shape, and location.

2. Background Art

Ulnar shortening osteotomies have been performed by surgeons for decades to address ulnocarpal impaction. More recently, a less invasive technique has been developed that involves the strategic removal of 2-5 mm of the ulna at its neck region.

Heretofore, it has been common to perform this procedure freehand with a motorized saw. The optimal cutting location is identified primarily visually by the surgeon, who makes an initial cut along a first line. A subsequent cut is made gauged from the location of the first cut to separate a bone fragment. The ulnar surfaces formed by the separate cuts are then drawn together. The separate bone parts, on which the surfaces are formed, are thereafter maintained together using headless screws.

Heretofore, ulnar shortening osteotomies have been performed without the use of guides. While surgeons skilled in this field may be capable of determining the optimal location of the cuts without any significant preoperative analysis, the ability to precisely locate the cuts and remove the optimal amount of bone are often dependent upon the skill of the surgeon, who must control the cutting tool relying primarily on visual reference. This may lead to situations where more or less than an optimal amount of bone is initially removed. In the latter case, one or more additional cuts may be required, thereby complicating the procedure. In the former case, the ultimate effectiveness of the procedure may be compromised.

Further, unguided cutting may produce irregular surfaces on the separate bone parts that do not precisely match when they are drawn together. This may result in a deviation from the desired degree of shortening. This may also adversely affect the time of healing and/or the effectiveness of the fusion of the bone parts.

In spite of the limitations of existing procedures, the industry has continued to perform ulnar shortening osteotomies relying primarily upon the observations of the surgeon and his/her skill and dexterity in manipulating cutting tools.

SUMMARY OF THE INVENTION

In one form, the invention is directed to a method of performing an osteotomy. The method includes the steps of: a) providing a guide assembly; b) placing the guide assembly in operative relationship to a bone to be cut so that the guide assembly defines first and second guide edges that are in fixed relationship to each other to each guide movement of a cutting tool; c) guiding the cutting tool along each of the first and second guide edges to produce first and second cut lines in the bone to facilitate separation and removal of a fragment of the bone from between first and second bone surfaces formed respectively at the first and second cut lines; d) separating the bone fragment so that a gap with a first width is formed between the first and second bone surfaces; and e) changing the width of the gap to be less than the first width.

In one form, the method of performing an osteotomy further includes the step of providing a base assembly that, in conjunction with the guide assembly, makes up a first subassembly. The first subassembly is placed in an operative state wherein the base assembly is secured to the bone and the guide assembly is attached to the base assembly with the guide assembly in the operative relationship to the bone.

In one form, the step of providing a guide assembly involves providing a guide assembly having a body on which the first and second guide edges are defined with a permanently fixed first angular relationship.

In one form, the method of performing an osteotomy further includes the step of providing first and second guide assemblies. Each guide assembly has a body on which first and second guide edges are defined with a permanently fixed angular relationship. The permanently fixed angular relationship of the first and second guide edges on the first guide assembly is different than the permanently fixed angular relationship of the first and second guide edges on the second guide assembly. The step of providing a guide assembly involves selecting a guide assembly from between the first and second guide assemblies based upon a desired permanently fixed angular relationship between the first and second guide edges.

In one form, the guide assembly is fully separable from the base assembly.

In one form, the method of performing an osteotomy further includes the steps of providing a positioning guide and placing the positioning guide against the bone to align the base assembly in a position desired for the base assembly relative to the bone with the first subassembly in the operative state.

In one form, the positioning guide is fully separable from the base assembly.

In one form, the method of performing an osteotomy further includes the step of providing a base assembly that in conjunction with the guide assembly makes up a first subassembly. The first subassembly has different operative states wherein the guide assembly is in its operative relationship to the bone. The first and second guide edges have a first angular relationship with the first subassembly in a first operative state and a second angular relationship that is different than the first angular relationship with the first subassembly in a second operative state. There is a first guide part on the first subassembly that is: a) releasably maintained in a first position relative to the bone with the first subassembly in the first operative state; and b) movable from the first position into a second position, in which the first guide part can be releasably maintained, with the first subassembly in the second operative state.

In one form, the first guide part pivots around an axis as it is moved between the first and second positions.

In one form, the step of changing the width of the gap involves using a separate instrument to engage bone parts on opposite sides of the gap and produce forces on the bone parts that cause the first and second bone surfaces to be urged towards each other.

In one form, the separate instrument has an associated ratchet mechanism through which different forces can be generated and maintained that cause the first and second bone surfaces to be urged towards each other.

In one form, the first guide part is releasably maintained in the first and second positions through a ratchet mechanism.

In one form, the method of performing an osteotomy further includes the step of directing a fixation component through the first and second bone surfaces, after the width of the gap is reduced, to place first and second bone parts on which the first and second bone surfaces are respectively formed in a final desired relationship wherein the first and second surfaces are either against or adjacent to each other. The fixation component maintains the first and second bone parts in the final desired relationship.

In one form, the first guide part pivots relative to a second guide part on the first subassembly. A holding assembly acts directly between the first and second guide parts and maintains the first and second guide parts in at least one relationship.

In one form, the method of performing an osteotomy further includes the steps of providing a guide assembly on the first guide part and, by using the guide assembly, controllably directing a fixation component through the first and second base surfaces after the width of the gap is reduced. The first and second bone parts on which the first and second bone surfaces are respectively formed are thereby placed in a final desired relationship wherein the first and second surfaces are either against or adjacent to each other. The fixation component maintains the first and second bone parts in the final desired relationship.

In one form, first and second surfaces are defined respectively on first and second bone parts. The method of performing an osteotomy further includes the step of providing a holding assembly that acts between the first and second bone parts to maintain the bone parts in a relationship wherein the first and second surfaces are either against or adjacent to each other.

In one form, the holding assembly acts between the first and second bone parts so that the first and second bone surfaces are urged towards each other.

In one form, one of the base assembly and guide assembly has a post with an axis and the other of the base assembly and guide assembly has a receptacle for the post. The base assembly and guide assembly are engageable and separable by being translated relative to each other along the post axis by respectively directing the post into the receptacle and withdrawing the post from the receptacle.

In one form, one of the positioning guide and base assembly has a post with an axis and the other of the positioning guide and base assembly has a receptacle for the post. The positioning guide and base assembly are engageable and separable by being translated relative to each other along the post axis by respectively directing the post into the receptacle and withdrawing the post from the receptacle.

In one form, the step of changing the width of the gap involves using an instrument with first and second parts respectively on first and second bone parts on which the first and second bone surfaces are respectively formed in a manner so as to cause the first and second bone surfaces to be moved against or adjacent to each other. The first instrument part has a guide assembly. The method of performing an osteotomy further includes the step of using the guide assembly to controllably direct a fixation component through the first and second bone surfaces after the width of the gap is reduced to maintain the first and second bone surfaces against or adjacent to each other.

DETAILED DESCRIPTION OF THE PREFERRED EMBODIMENT

Figure 1:
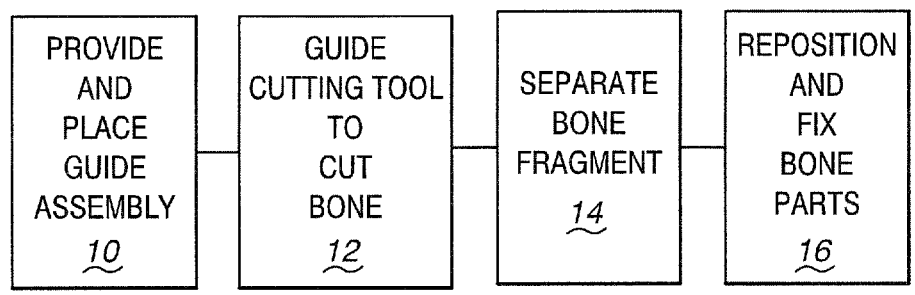
FIG. 1 is a flow diagram representation of a method of performing an osteotomy, according to the present invention.
Figure 2:
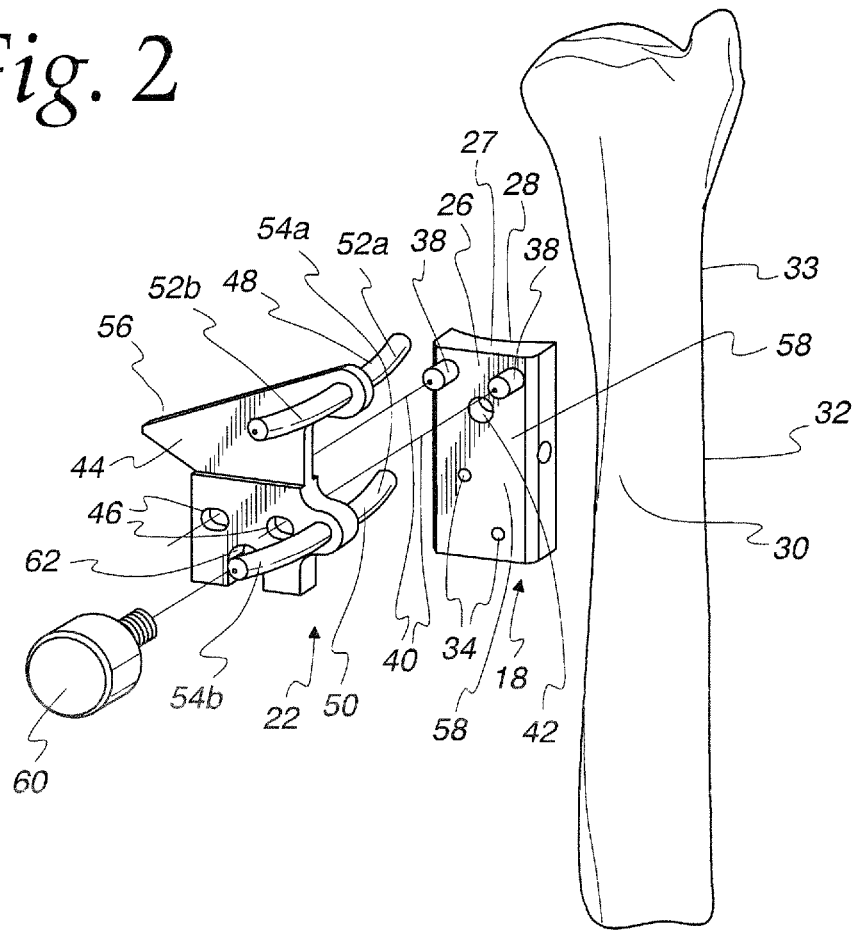
FIG. 2 is an exploded perspective view of a portion of an ulnar bone with a base assembly, according to the invention, for attachment to the ulnar bone and a positioning guide that facilitates strategic placement of the base assembly.
Figure 3:
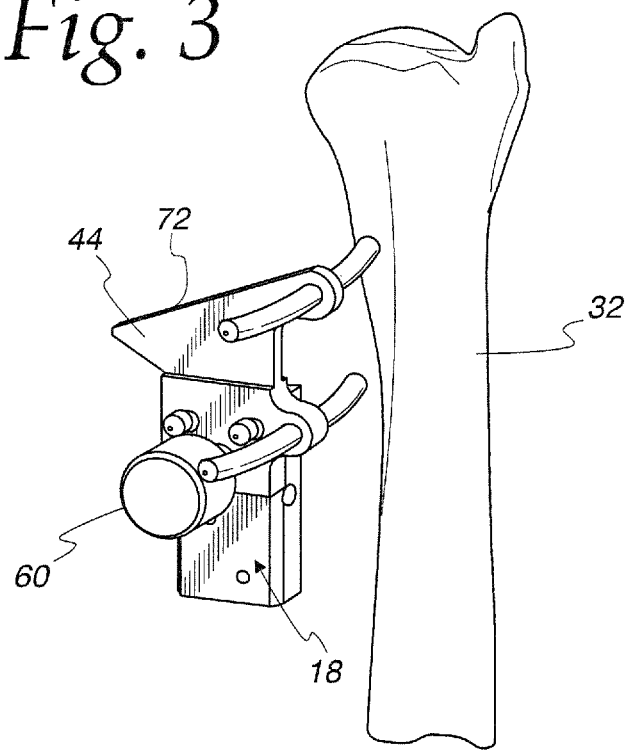
FIG. 3 is a view as in FIG. 2 with the base assembly and positioning guide joined but remaining separate from the ulnar bone.

In FIG. 1, a flow diagram representation of a method of performing an osteotomy, according to the present invention, is shown. According to the invention, a guide assembly is provided and placed in operative relationship to a bone to be cut, such as an ulnar bone, as shown at block 10 in FIG. 1. The guide assembly defines first and second guide edges that are in fixed relationship to each other to guide movement of a cutting tool.

As shown at block 12, the cutting tool is guided along each of the first and second guide edges to cut the bone so as to produce first and second cut lines in the bone to facilitate separation and removal of a wedge-shaped fragment of the bone from between first and second bone surfaces formed at the separate cut lines.

As shown at block 14, the bone fragment defined by using the cutting tool is separated and removed so that a gap of a first width is formed between the first and second bone surfaces.

Separate bone parts, upon which the first and second bone surfaces are formed, are repositioned to reduce the width of the gap, after which the bone parts are fixed for healing, as shown at block 16.

The inventive method will be described hereinbelow with respect to exemplary components that are suitable for its practice. The schematic showing of the method in FIG. 1 is intended to encompass use of the specific components described herein and use of virtually an unlimited number of variations thereof, consistent with the inventive concepts. The precise nature of the components and manner of carrying out the inventive method, described hereinbelow, are exemplary in nature only and should not be considered limiting.

One form of the invention will be described with reference to FIGS. 2-12. To perform the method, there are four basic components utilized: a) a base assembly 18; b) a guide assembly 20; c) a positioning guide 22; and d) a combined clamp and drill guide assembly 24. Not all of these components are required to carry out the inventive method, in its most basic form. Further, components additional to those shown may be utilized.

The base assembly 18 has a body 26 with an upper surface 27 and a curved mounting surface 28 that is nominally matched to an exposed surface 30 on an ulnar bone 32. The mounting surface 28 is also nominally matched to the opposite exposed ulnar surface 30, whereby the base assembly 18 can be mounted on either side of the ulnar bone 32 upon which the procedure is performed.

The body 26 has a pair of openings 34, each to receive a fixation component 36. The axes of the openings 34 are preferably at an angle to each other so that the fixation components 36 are not in parallel relationship, whereby potentially greater stability for the base assembly mounting is made possible.

The base assembly 18 has a pair of cantilevered posts 38 with substantially parallel axes 40. The base assembly 18 further has a component mounting opening 42 in the body 26.

The positioning guide 22 is connected to the base assembly 18 to facilitate strategic placement of the base assembly 18 so that it will support the guide assembly 20 appropriately to facilitate controlled and precise cutting of the ulnar bone 32 at precisely the desired location. The positioning guide 22 has a body 44 with receptacles 46, in the form of throughbores, to receive the posts 38.

The positioning guide 22 further has spaced guide pegs 48, 50 at spaced locations upon the body 44. The guide peg 48 has straight portions 52a, 52b projecting oppositely away from the body 44. The guide peg 50 has curved portions 54a, 54b also projecting oppositely away from the body 44. The positioning guide 22 is symmetrical about a plane within which the flat aspect of the body 44 resides, thereby to allow the same positioning guide 22 to be used with the base assembly 18 mounted on either side of the ulnar bone 32.

The positioning guide 22 and base assembly 18 are engageable and separable by being translated relative to each other parallel to the post axes 40, with the posts 38 aligned one each with the receptacles 46. With the positioning guide 22 and base assembly 18 engaged, a substantially flat surface 56 on the positioning guide 22 facially abuts to a substantially flat surface 58 on the base assembly 18. The base assembly 18 and positioning guide 22 are maintained together using a fastener 60 that is directed through an opening 62 in the positioning guide 22 and into the mounting opening 42 in the base assembly 18. The connection may be maintained using cooperating male and female threads or any other type of releasable connection well known to those skilled in this art. The fastener 60 and posts 38 create a three-point connection arrangement that positively maintains the desired orientation between the joined positioning guide 22 and base assembly 18. The nature of the fastener may be different than what is depicted or alternatively the fastener may be eliminated, with the components thereby held in place through frictional forces.

It should be understood that while the posts 38 are shown on the base assembly 18, they might alternatively be provided upon the positioning guide 22, or other components described hereinbelow that cooperate with the base assembly 18. The cooperating receptacles would then be provided on the base assembly 18.

Figure 4:
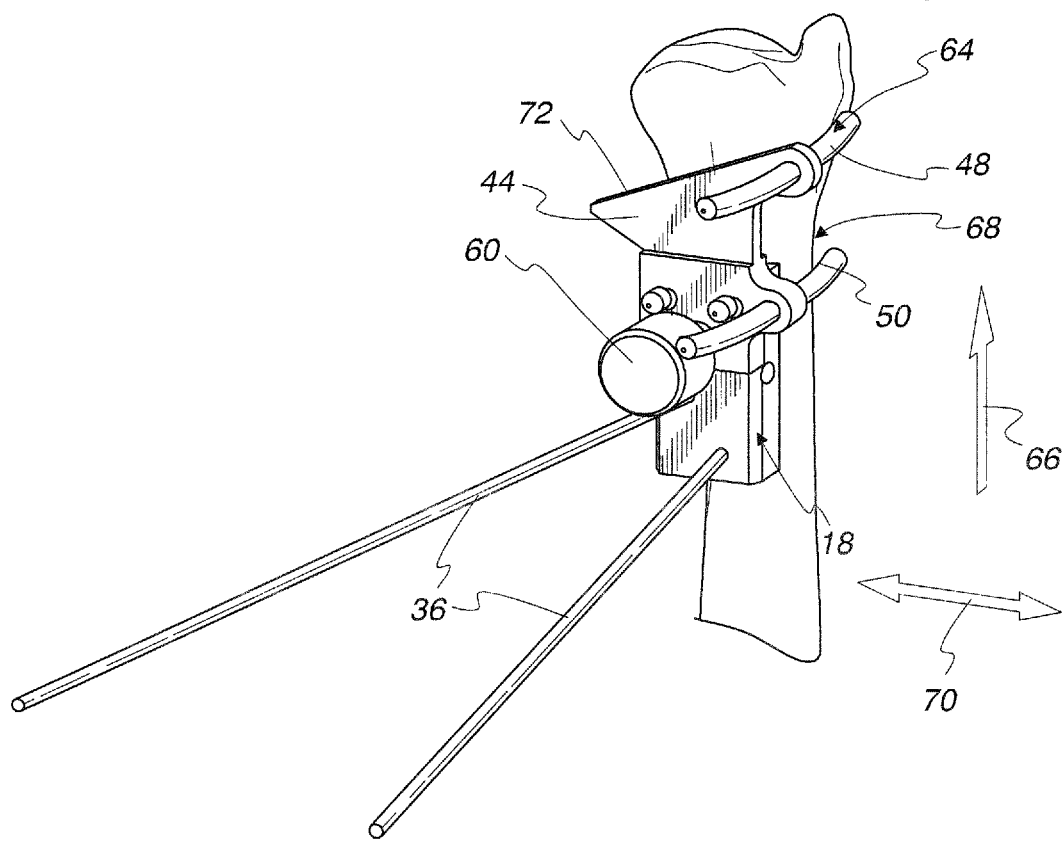
FIG. 4 is a view as in FIG. 3 with the joined base assembly and positioning guide secured to the ulnar bone.
Figure 5:
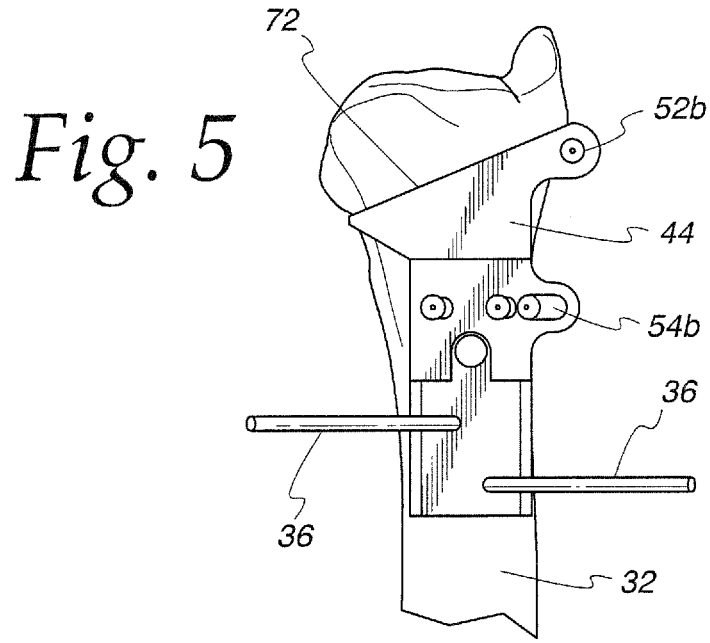
FIG. 5 is a side elevation view of the components in FIG. 4.
Figure 6:
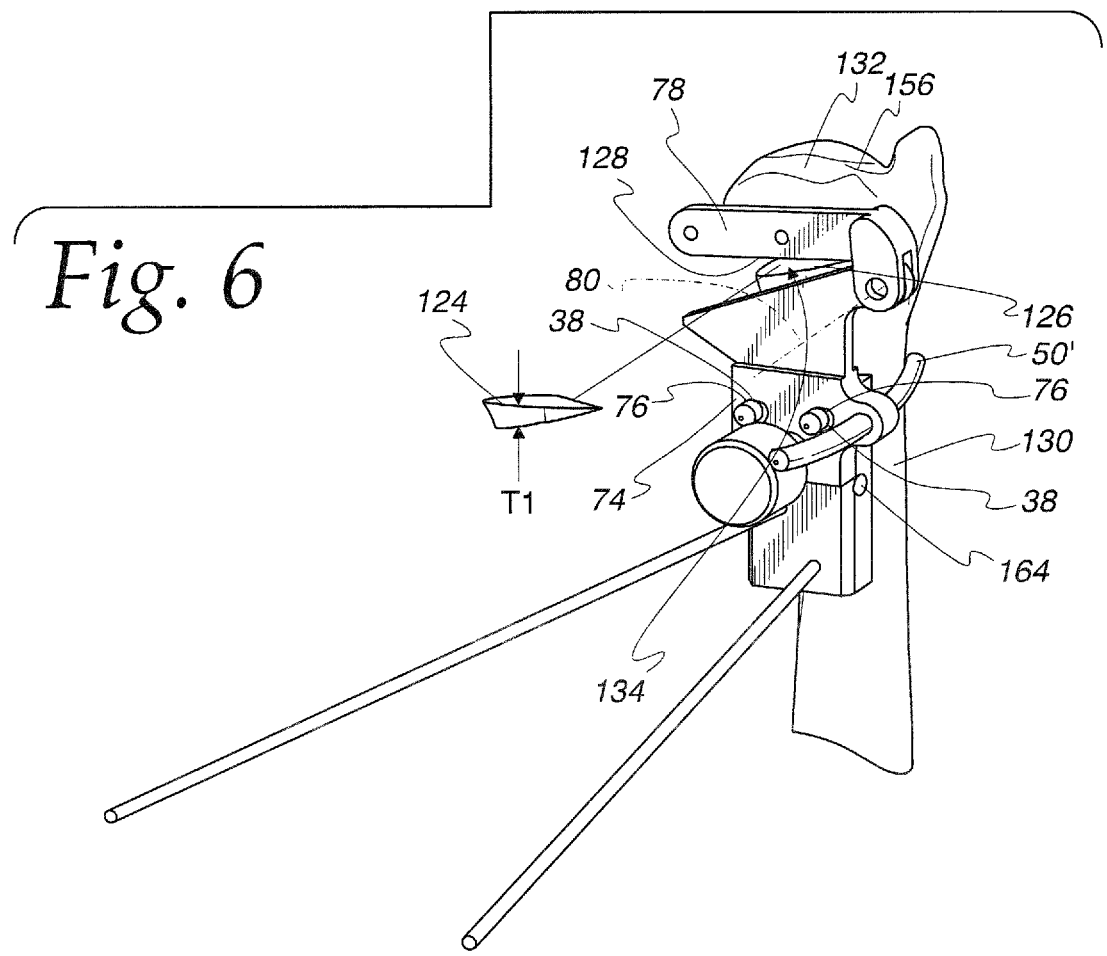
FIG. 6 is a view as in FIG. 4 wherein a guide assembly, according to the invention, has been substituted for the positioning guide.
Figure 7:
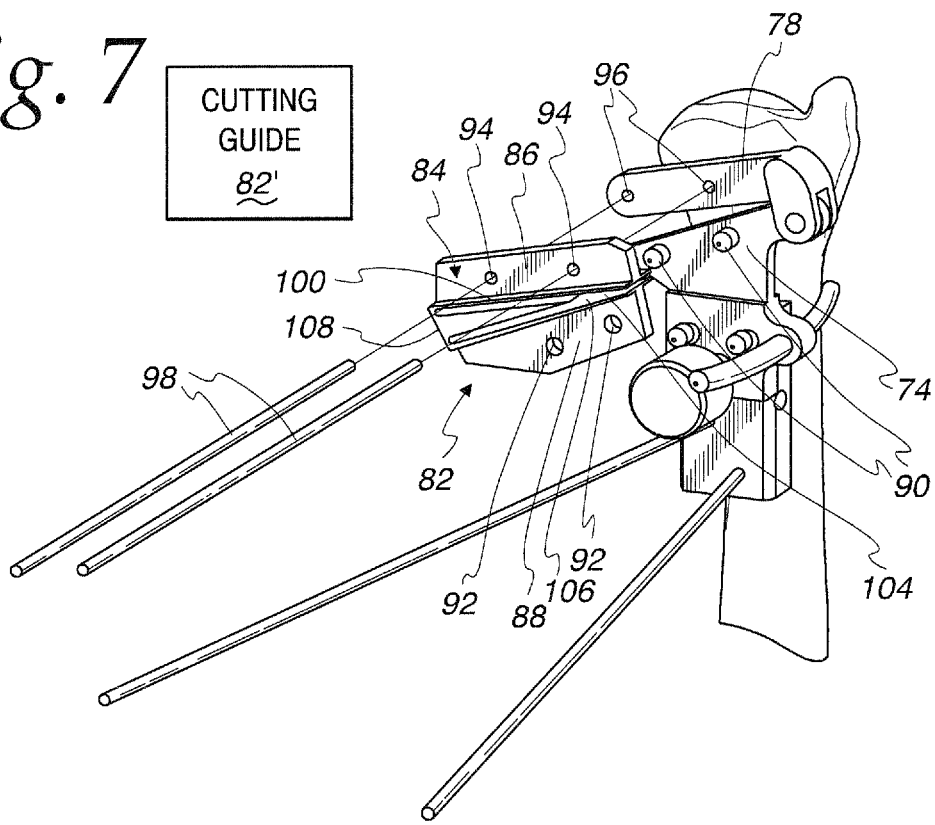
FIG. 7 is a view as in FIG. 6 and showing interchangeable cutting guides usable with the guide assembly.
Figure 8:
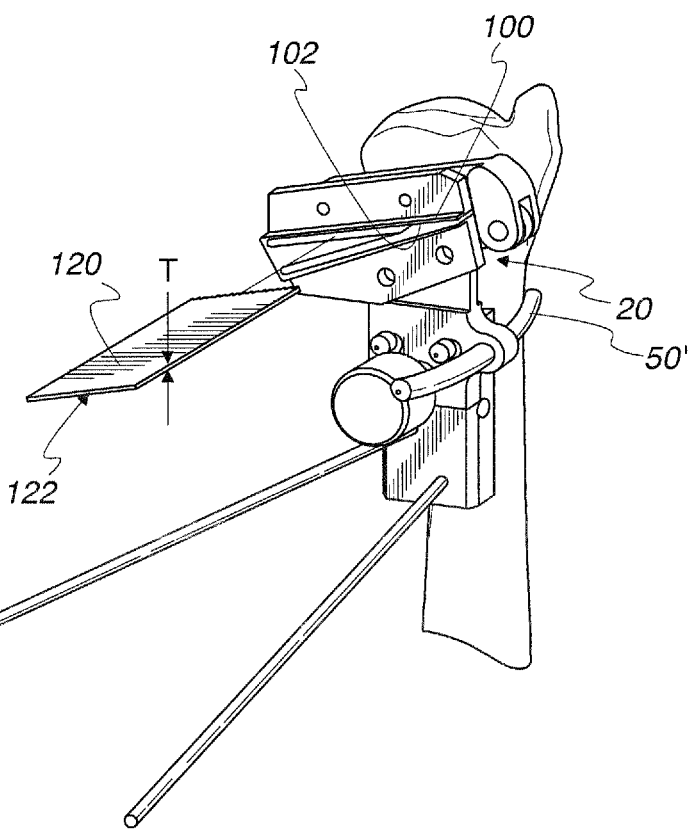
FIG. 8 is a view as in FIG. 7 with one of the cutting guides in place.
Figure 9:
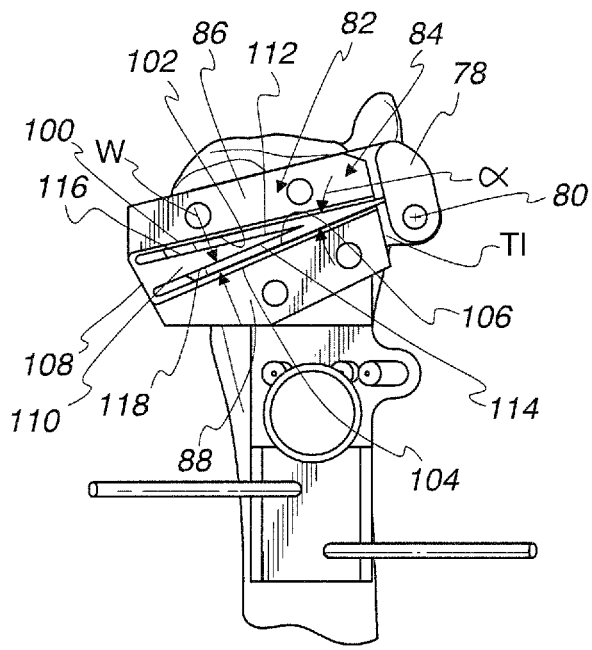
FIG. 9 is a side elevation view of the components in FIG. 8.

With the positioning guide 22 and base assembly 18 engaged, the combined structure can be placed against the ulnar bone 32 as shown in FIGS. 4-6. The body 26 is configured so that the upper surface 27 thereon engages a patient's cartilage to block movement of the body 26 consistently in its optimal location along the length of the ulnar bone 32 as it is translated along the ulnar bone 32 in the direction of the arrow 66 in FIG. 4.

The guide peg 48 engages an ulnar region at 64 to consistently locate one end of the combined structure in the optimal position along the line indicated by the arrow 70, that is orthogonal to the line indicated by the arrow 66, which is parallel to the length of the ulnar bone 32 in FIG. 4. The guide peg 50 is curved to conform nominally to the shape of the ulnar region at 68 and abuts thereto to function together with, and in the same manner as, the guide peg 48 to positively and consistently align both ends of the combined structure along the line indicated by the arrow 70.

The base assembly 18 and positioning guide 22 are strategically constructed so that an edge 72 on the body 44 of the positioning guide 22 aligns over the ulnar bone 32 where one of the cuts will be made during the procedure, thereby to allow the surgeon to visually verify proper locational securement of the base assembly 18. The edge 72 may have different angles relative to the length of the ulnar bone 32 and may have a substantially orthogonal relationship. The fixation components 36 are then directed into the ulnar bone 32, whereupon the fastener 60 can be released to allow separation of the positioning guide 22 from the base assembly 18. Alternatively, the positioning guide 22, or a substitute structure that reinforces the base assembly 18 so as to maintain its alignment, can be left in place.

The guide assembly 20 is then mounted upon the base assembly 18 in the same manner that the positioning guide 22 is mounted to be placed in operative relationship to the ulnar bone 32. That is, the guide assembly 20 has a body 74 with round, or more preferably obround, receptacles 76 that receive the posts 38. The obround receptacles 76 allow fine adjustment of the guide assembly 20 along the line of the arrow 70 in FIG. 4 transversely to the length of the ulnar bone 32.

The guide assembly 20 has a first guide part 78 that is connected to a second part, in this case the body 74, for pivoting movement around an axis 80. The body 74 supports a guide peg 50' that has the same shape and function as the guide peg 50.

The guide assembly 20 further includes a separate cutting guide 82. The cutting guide 82 is preferably one of multiple cutting guides that are available and have different configurations, as explained hereinbelow. Another of the cutting guides is identified schematically at 82' in FIG. 7.

The cutting guide 82 has a body 84 with separate mounting blocks 86, 88. The cutting guide 82 is operatively mounted by directing spaced, cantilevered mounting posts 90 on the body 74, one each into throughbores/receptacles 92 on the mounting block 88.

The mounting block 86 has throughbores/receptacles 94 that are alignable, one each, with throughbores/receptacles 96 on the first guide part 78. Fixation components 98 are directed into the throughbores/receptacles 94, 96 to thereby secure the mounting block 86 to the first guide part 78.

The mounting block 86 is integrally formed with a flat plate 100 that has a flat surface/edge 102, hereinafter referred to as the "guide edge" 102. The mounting block 88 is likewise integral with a flat plate 104 that has a flat surface/edge 106, hereinafter identified as the "guide edge" 106.

The combined mounting block 86 and flat plate 100 and combined mounting block 88 and flat plate 104 are joined through a connecting part 108 that extends to form a wedge-shaped component 110 with surfaces/edges 112, 114 respectively spaced from and parallel to the cutting edges 102, 106. The edges 102, 112 cooperate to produce a guide slot 116, with the edges 106, 114 cooperating to produce a guide slot 118. The guide slots 116, 118 are at an angle a with respect to each other. The guide slots 116, 118 have a width W that is slightly greater than the thickness T of a toothed blade 120 on a cutting tool 122. The cutting blade 120 can thus be guided in two straight line paths within the guide slots 116, 118 by and between the edges 102, 112; 106, 114, with the angle a therebetween selected to determine the dimensions of a bone fragment 124 that is separated by the cutting tool 122 for removal by reason of the cutting tool 122 being moved guidingly along both of the slots 116, 118. By increasing the angle α, the thickness T1 of the bone fragment 124 is increased, which results in a greater degree of shortening of the ulnar bone 32, as explained further hereinbelow.

The invention contemplates that the guide slots 116, 118 can have a captured or non-captured construction. One or both of the edges 102, 112; 106, 114 may be used to guide the cutting tool 122 in each slot 116, 118.

The cutting guide 82', which is designed to be interchangeably usable with the cutting guide 82, has preferably a different angular relationship between corresponding guide slots 116, 118. An exemplary practical selection of the cutting guides would include four cutting guides with configurations to make 2 mm, 3 mm, 4 mm, and 5 mm cuts. This dimension is measured at the thickest portion of the wedge-shaped bone fragment 124.

In this embodiment, the slots 116, 118 are closed by the connecting portion 108 at one end of the slots 116, 118 and by the body 74 and first guide part 78 at the other end of the slots 116, 118. Accordingly, the cutting blade 120 is confined in its range of movement lengthwise along the slots 116, 118 and is consistently oriented and controllably guided in paths dictated by the slots 116, 118. The slots 116, 118 are utilized to make separate cuts that form substantially flat and angled surfaces 126, 128 on bone parts 130, 132, respectively. With the bone fragment 124 removed, the surfaces 126, 128 bound a gap 134 initially corresponding to the configuration of the removed bone fragment 124 that is enlarged by the thickness T1 of the cutting blade 120. The surfaces 126, 128 formed at the cut lines reside in planes that are substantially parallel to the post axes 40.

The base assembly 18 and guide assembly 20 together make up a first subassembly that has different operative states with the guide assembly 20 in operative relationship to the ulnar bone 32. With the cutting guide 82 utilized, the first subassembly is in a first operative state wherein the guide edges 102, 106 have a first angular relationship. With the cutting guide 82' utilized, the first subassembly has a second operative state, wherein the corresponding guide edges have a different angular relationship.

With the separate cut lines produced in the bone and the bone fragment 124 removed to create the gap 134, the bone parts 130, 132 can be acted upon so as to cause the surfaces 126, 128 to be urged either against or adjacent to each other. With the bone fragment 124 removed, the bone parts 130, 132 remain joined at the location at 135, which functions as a hinge as the gap 134 is closed. The hinge will confine relative movement of the bone parts 130, 132 substantially to about an axis so that the bone parts 130, 132 will not relatively twist about an axis extending lengthwise of the ulnar bone 32.

While the invention contemplates that a separate instrument need not be connected to the base assembly 18 to accomplish this, in a preferred form, the aforementioned combined clamp and drill guide assembly 24 functions as such an instrument. The combined clamp and drill guide assembly 24 is made with a scissors-type configuration with elongate legs 136, 138 hinged mid-length for relative movement about an axis 140. The leg 136 has a finger loop 142 at one end thereof and at its opposite end a post 144 that is integral with a block 146 that is connected to the leg 136 for pivoting movement around an axis 148 that is parallel to the axis 140.

The leg 138 has a finger loop 150 at one end and a drill guide 152 at its opposite end. The drill guide 152 has a housing 154 that bears against the end 156 of the ulnar bone 32 and also defines a guide receptacle 158 for a drill guide 160. The drill guide 160 is aligned on the housing 154 so that a central axis 162 thereof is substantially orthogonal to the surface 126 on the bone part 132.

The post 144 is directed into a receptacle 164 on the base assembly 18. With this arrangement, by engaging the finger loops 142, 150, as one would the loops on a scissors, the loops 142, 150 can be urged towards each other, thereby drawing the housing 154 towards the post 144. This produces a captive/clamping force upon the bone parts 130, 132, urging them towards each other so as to bring the bone surfaces 126, 128 either against each other or into close proximity.

A conventional ratchet mechanism/holding assembly is provided at 166 on the legs 136, 138 to allow a progressively increasing force to be developed and maintained as the loops 142, 150 are urged towards each other. Through this arrangement, a progressively increasing force is generated upon the bone parts 130, 132 until they are caused to achieve a final desired relationship.

Instead of being directed into the receptacle 164 on the base assembly 18, the post 164 can be borne against the guide peg 50', otherwise corresponding in structure and function to the guide peg 50.

Figure 10:
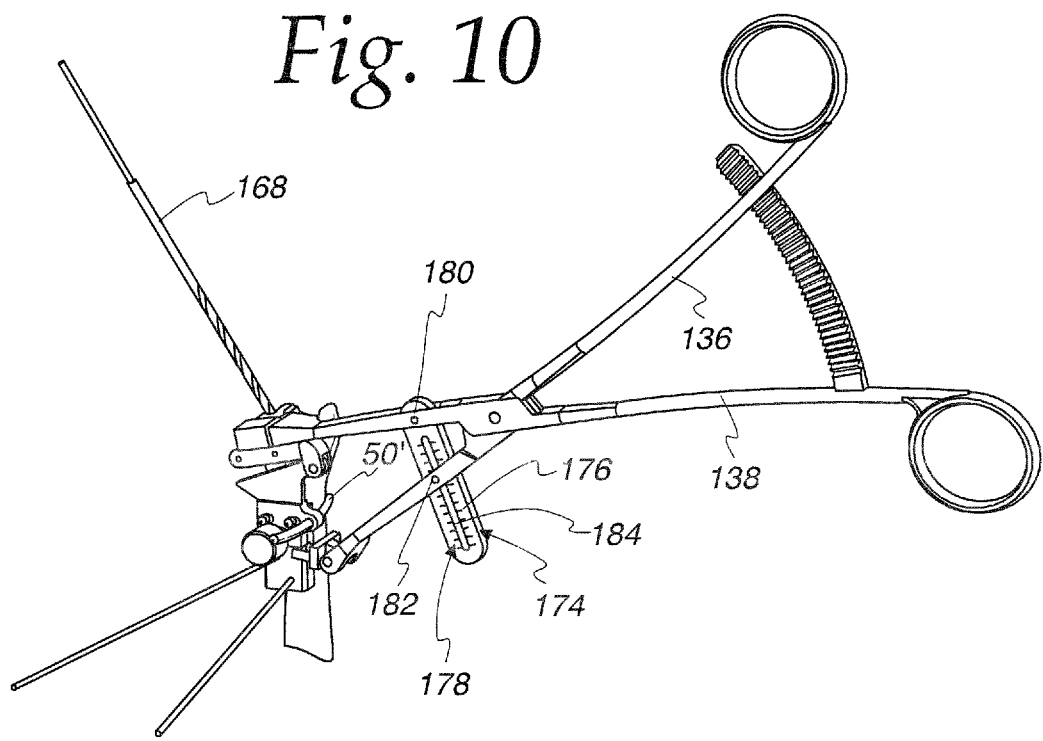
FIG. 10 is a view as in FIG. 6, reduced, and wherein an instrument, that makes up part of a combined clamp and drill guide assembly, is engaged and showing a drill bit directed into a drill guide thereon.
Figure 11:
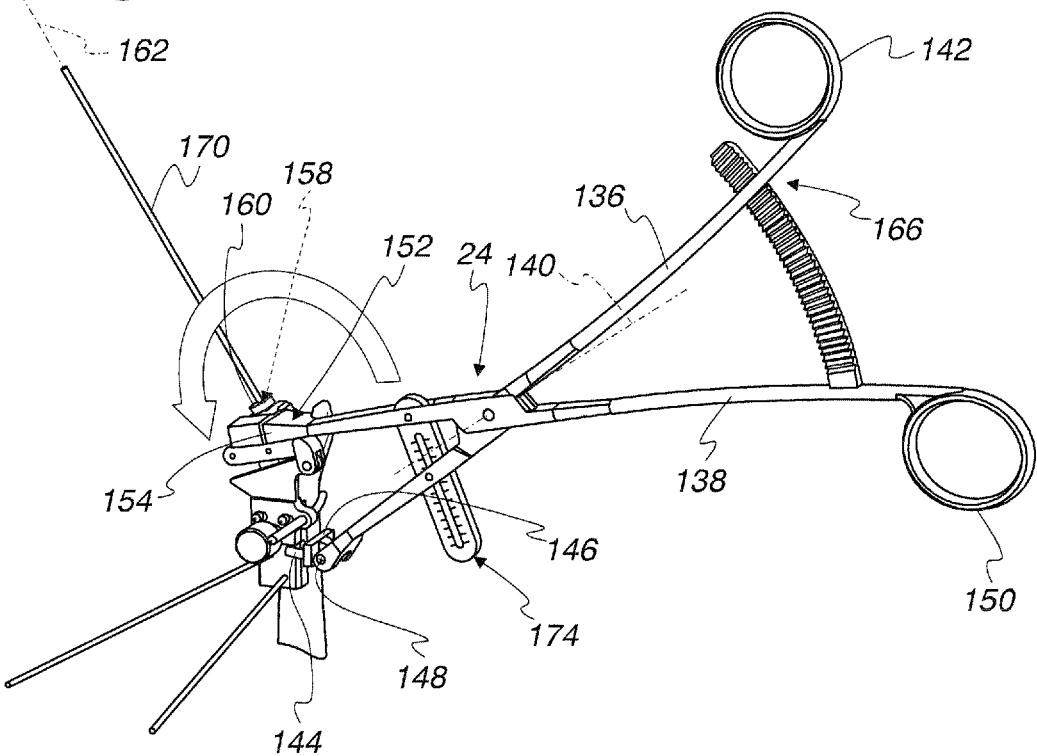
FIG. 11 is a view as in FIG. 10 wherein a guide for a fixation component is directed through a bore produced by the drill bit in FIG. 10.

As shown in FIG. 10, a drill bit 168 can be directed into the drill guide 152 and advanced along the axis 162 to bore successively through the bone part 132, through the surfaces 126, 128, and into the bone part 130. An elongate guide component 170 can then be directed through the bore made by the drill bit 168, as shown in FIG. 11, after which a threaded fixation component 172 can be placed over the guide component 170 and progressively threaded through the bone part 132 and into the bone part 130 to thereby maintain the bone parts 130, 132 in a final desired relationship.

The combined clamp and drill guide assembly 24 functions as a holding assembly that acts between the bone parts 130, 132 to maintain a final desired relationship while the fixation component 172 is put in place.

In a preferred form, more than one fixation component 172 would be directed into the bone parts 130, 132. The additional fixation components 172 would be implanted in the same manner that the first described fixation component 172 is implanted.

A gauge 174 is provided on the combined clamp and drill guide assembly 24 to allow visual identification of the ulnar shortening that has occurred. The gauge 174 consists of a flat plate 176 with graduations 178 thereon. The plate 176 is joined to the leg 138 through a pivot pin 180. A pivot pin 182 extends through the leg 136 and into a guide slot 184 in the plate 176. A quantifiable correlation exists between: a) the relationship between the leg 136 and graduations 178; and b)

the distance from the ulnar end to and through surfaces 126, 128. Through the gauge 174 the surgeon is allowed to identify the appropriate length of the fixation components 172 thereafter directed into the bone parts 130, 132 to maintain the final desired relationship therebetween.

Figure 13:
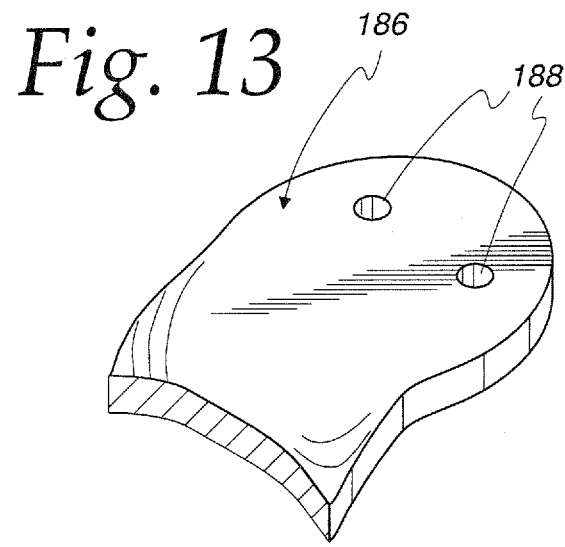
FIG. 13 is an enlarged, fragmentary, perspective view of a part of a clamp assembly to engage a bone surface.

In FIG. 13, a variation of a component that is on the leg 138 and engageable with the end of the ulnar bone 32 is shown at 186. The component 186 has a relatively thin profile and can be configured to conform to the contours of the end of the ulnar bone 32. The component 186 may be spatula-shaped with a wide footprint. The component 186 may be curved to articulate with the end of the ulnar bone 32 without causing any injury to it. Openings 188 are shown to allow passage therethrough of the aforementioned fixation component(s) 172. This component may have a dedicated clamp function or may be used in combination with a drill guide.

Once the bone parts 130, 132 have been fixed using the fixation components 172, the combined clamp and drill guide assembly 24 and base assembly 18 can be separated from the ulnar bone 32.

Figure 14:
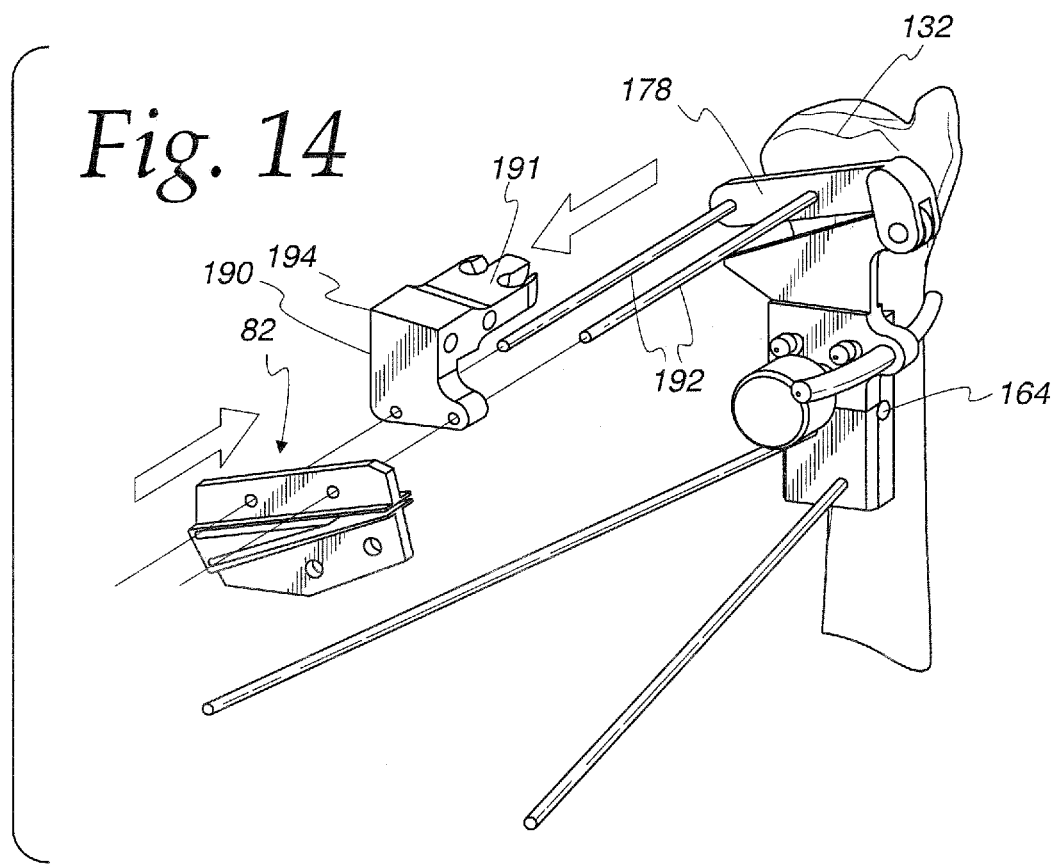
FIG. 14 is an exploded perspective view of the components as in FIG. 7 with a modified form of drill guide.
Figure 15:
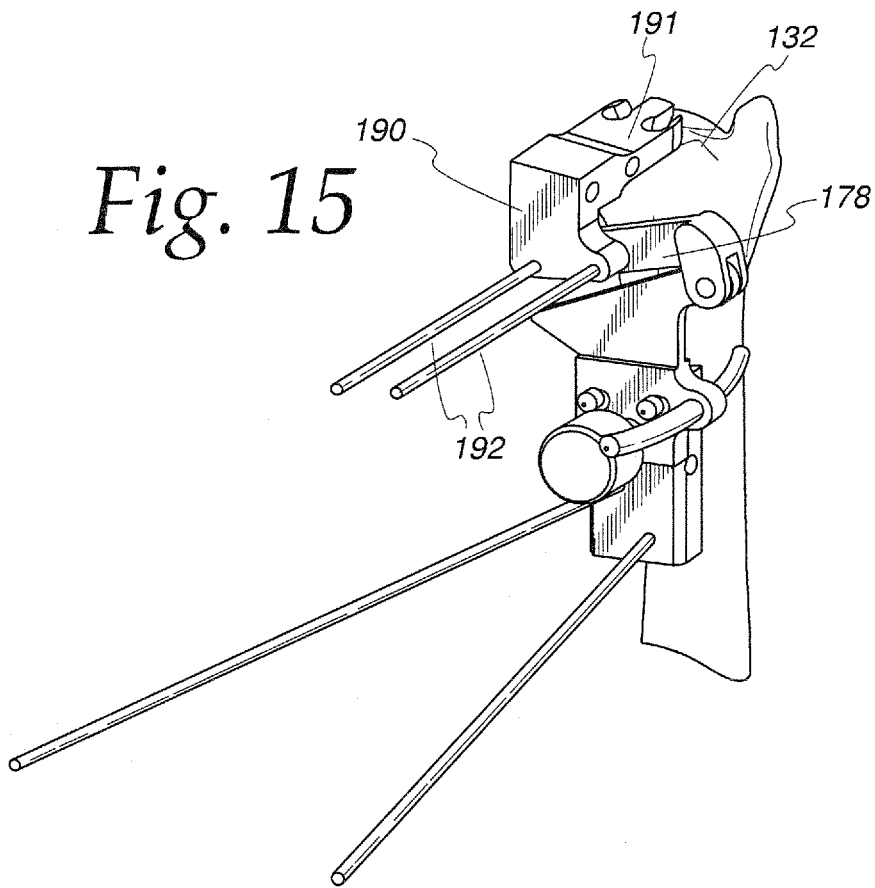
FIG. 15 is a view as in FIG. 14 with the drill guide in place.

A number of variations from the above-described method and components are contemplated. As one example, as shown in FIGS. 13 and 14, a reinforcing component 190 may be utilized to connect a drill guide 191 to the first guide part 178. Fixation components 192 can be directed through the reinforcing component 190 and into the first guide part 178. The fixation components 192 may be extended to penetrate the bone portion 132 to fix the location of the drill guide 191 and provide stability.

Figure 12:
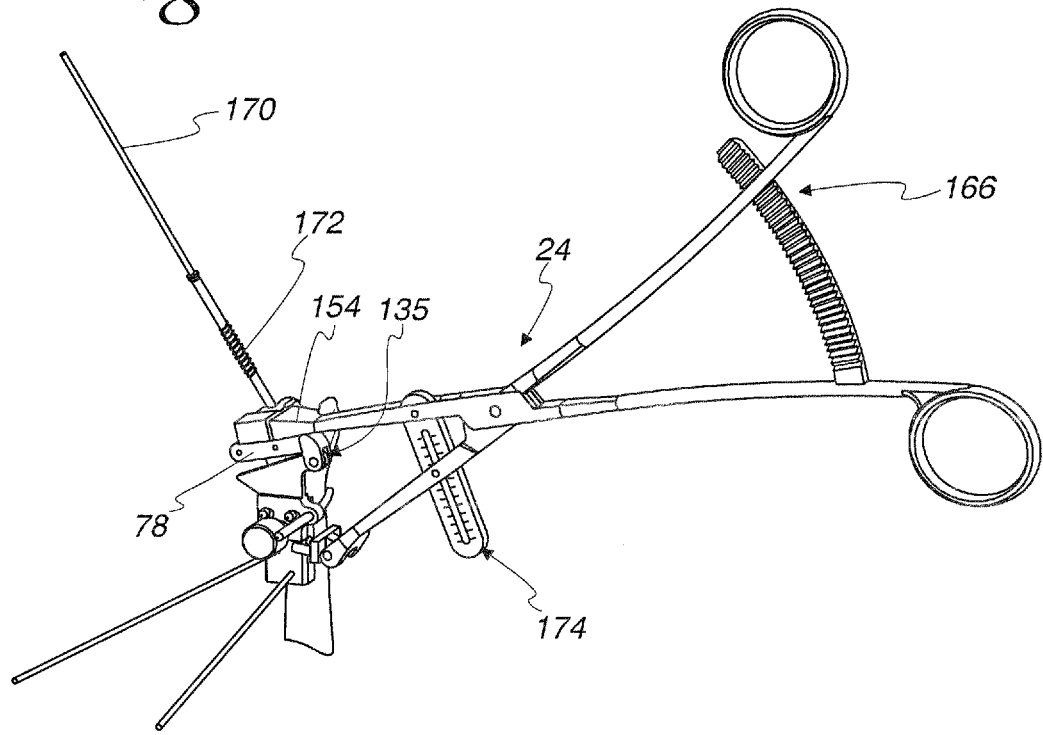
FIG. 12 is a view as in FIG. 11 wherein a fastener component is directed over the guide.
Figure 16:
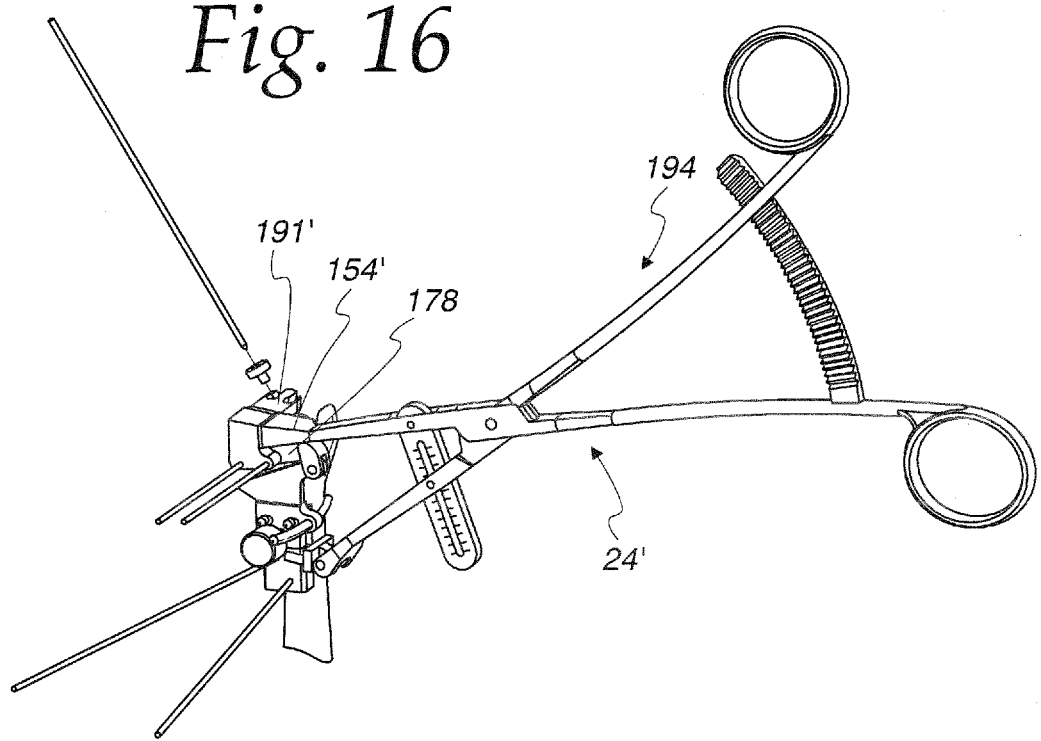
FIG. 16 is a view as in FIG. 15, reduced, and wherein an instrument as in FIGS. 10-12 is utilized to make up a clamp assembly.

In FIG. 16, a drill guide 191' is shown that can be attached to the first guide part 178 in the same manner, and as a substitute for, the drill guide 191. The drill guide 191' is combined with a clamping instrument 194 similar to what is shown in FIGS. 10-12, to function as part of a modified combined clamp and drill guide assembly 24'.

While it has been described that the positioning guide 22 is removed before putting the guide assembly 20 in place as noted above, it is possible to design the components so that the positioning guide remains in place at all times.

Figure 17:
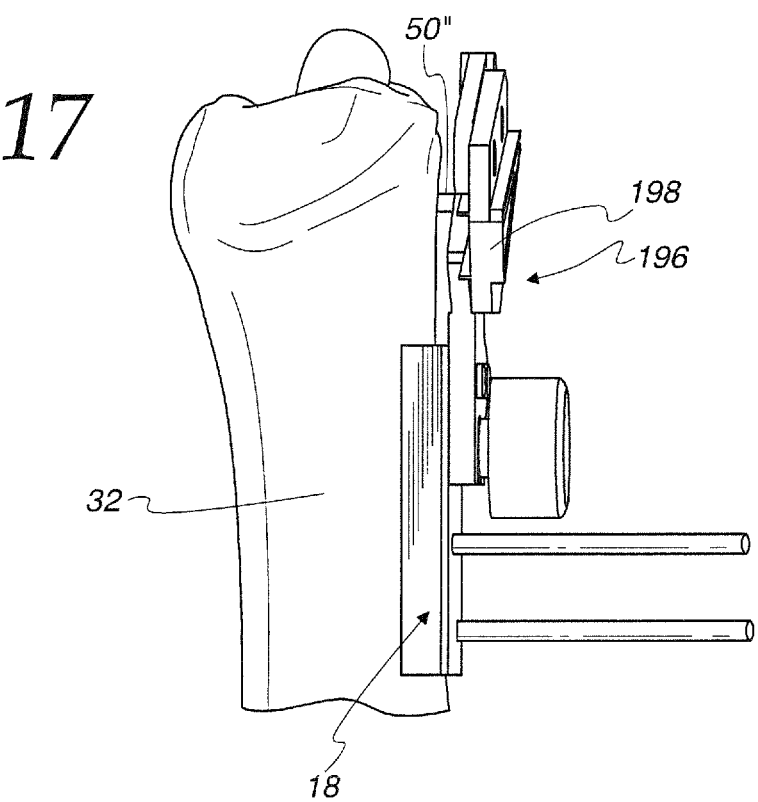
FIG. 17 is a fragmentary, side perspective view of a portion of an ulnar bone with a base assembly and modified form of guide assembly, according to the invention.
Figure 18:
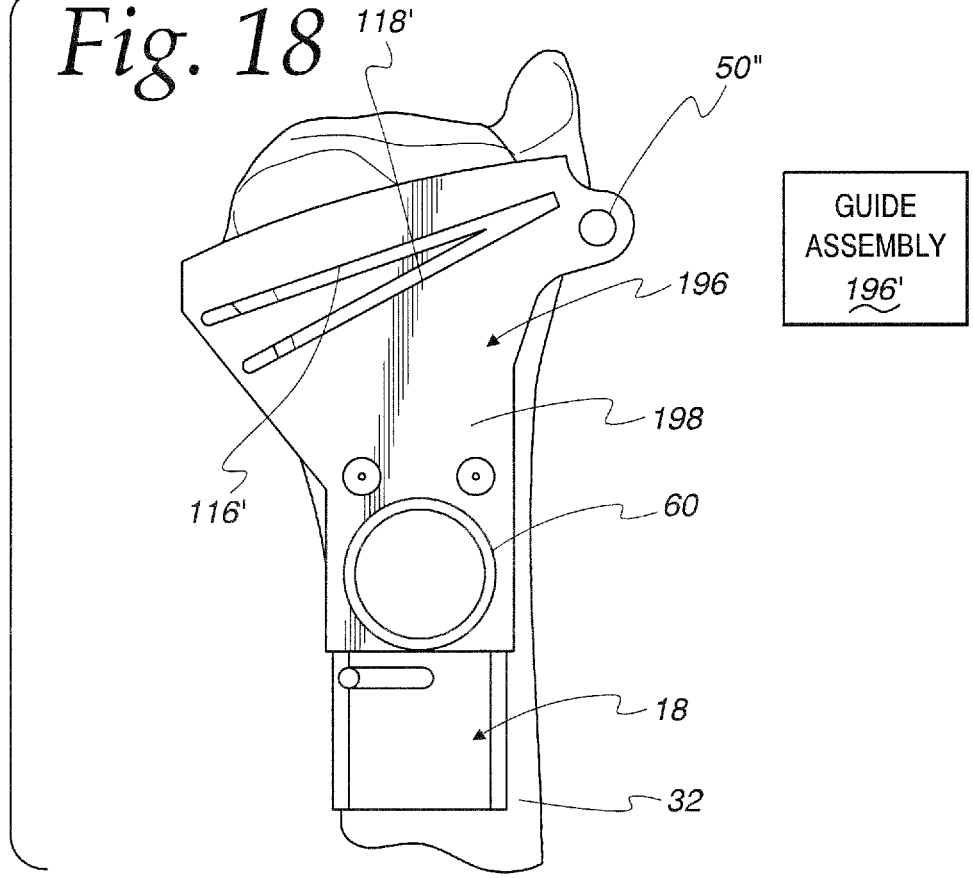
FIG. 18 is a view as in FIG. 17 with the components turned through 90°.

In FIGS. 17 and 18, a modified form of guide assembly is shown at 196 on the ulnar bone 32 to cooperate with the aforementioned base assembly 18. In this embodiment, a thickened body 198 is attached to the base assembly 18 and held with the fastener 60 in the same manner that the positioning guide 22 is attached. The body 198 is located precisely, and stabilized, by a guide peg 50", corresponding in structure and function to the guide pegs 50, 50', described above. Separate guide slots 116', 118' are formed, with a permanently fixed angular relationship, directly in the body 198.

At least one other guide assembly 196' is provided with a different configuration of slot, i.e., preferably with a different angular relationship between guide slots. The surgeon has the option of selecting the guide assembly 196, 196' with the preferred angular relationship between the guide slots and engaging the selected guide assembly with the base assembly 18.

Figure 19:
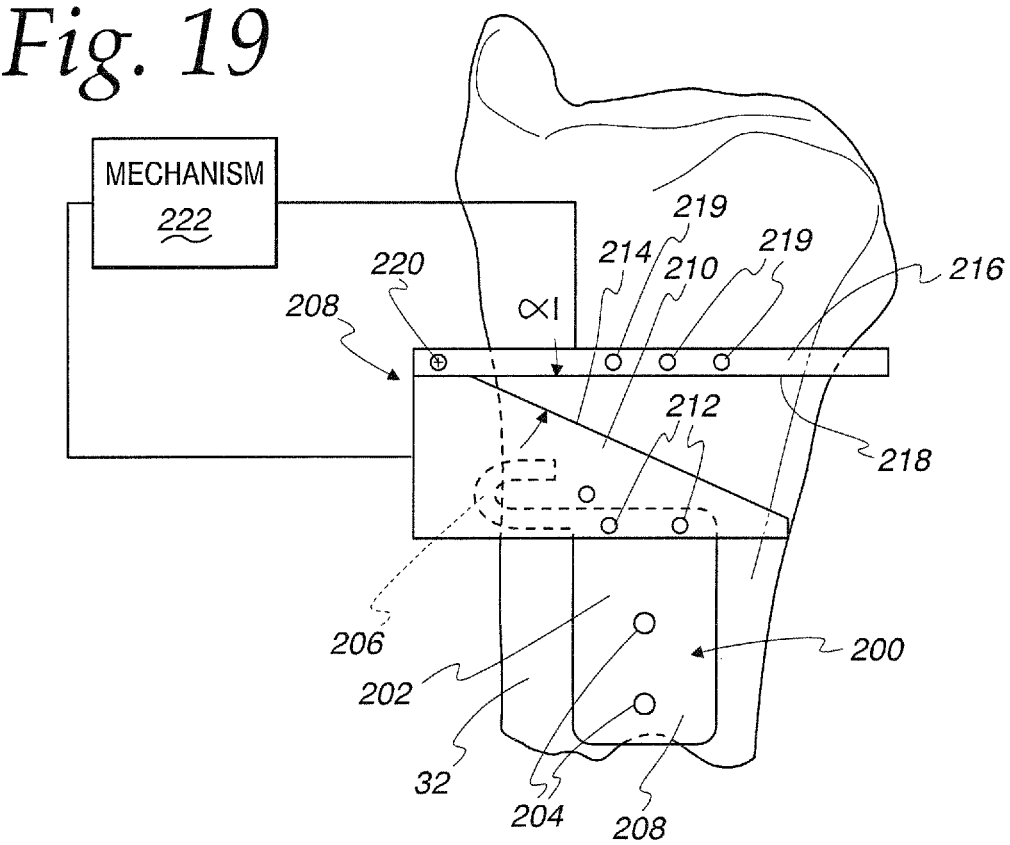
FIG. 19 is a fragmentary, elevation view of a further modified form of base assembly and guide assembly, according to the invention, in relationship to a portion of an ulnar bone.
Figure 20:
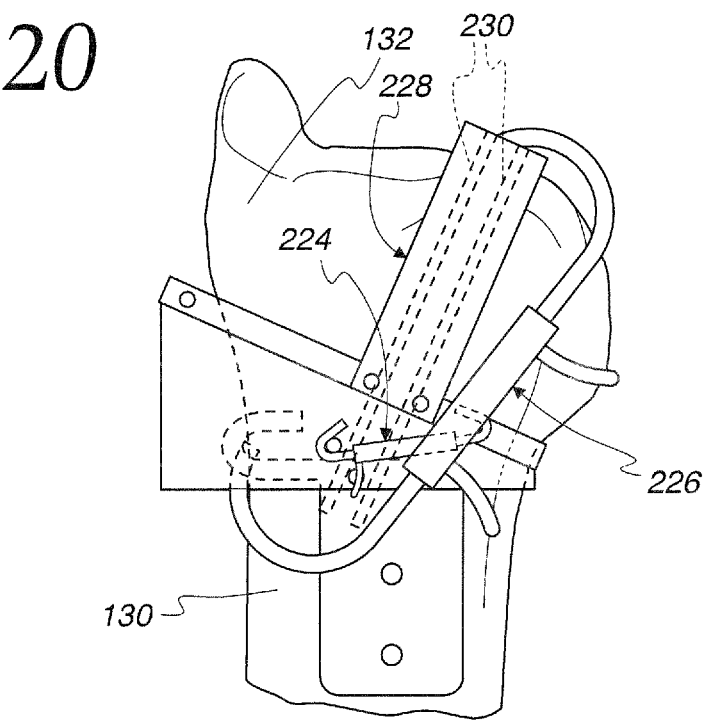
FIG. 20 is a view as in FIG. 19 and showing separate ratchet mechanisms for maintaining bone parts together after removal of a bone fragment and additionally showing a drill guide for facilitating insertion of a fixation component.

Further modified forms of base assembly, guide assembly, and combined clamp and drill guide assembly are shown in FIGS. 19 and 20.

A base assembly 200 has a body 202 that bears against the ulnar bone 32. Throughbores 204 accommodate fixation components, such as pins. The fixation components in this embodiment, as in the other embodiments, may have stops on them to maintain the body 202 against the ulnar bone 32.

The body 202 may have an ulnar sided extension 206 that may fit subperiosteally under the extensor carpi ulnaris (ECU) tendon and around the ulnar-sided cortex against this ulnar cortex. The extension 206 assists in both locating and stabilizing the body 202.

A guide assembly 208 consists of a guide part 210 that is fixed to the body 202 with fasteners (not shown) utilizing securing holes 212 in the body 202. The guide part 210 defines one cutting guide edge 214. A separate guide part 216 defines a separate cutting guide edge 218 and is fixedly connected to the ulnar bone 32 by fixation components (not shown) extending through securing holes 219 and is connected to the guide part 202 for pivoting movement relative thereto around an axis 220.

The guide assembly 208 and base assembly 200 together make up a first subassembly that has different operative states with the guide assembly 208 in operative relationship to the ulnar bone 32. The guide edges 214, 218 have a first angular relationship with the first subassembly in a first operative state and a second angular relationship, that is different than the first angular relationship, with the first subassembly in a second operative state. These different angular relationships produce different angles al between the cutting guide edges 214, 218 that is changed by pivoting the guide part 216 relative to the guide part 210.

Through an appropriate mechanism/holding assembly 222, the first subassembly is releasably maintained in different operative states. In one form, the mechanism 222 is in the form of a holding assembly that acts directly between the guide part 216 and the guide part 210.

The mechanism 222 may be designed to set and maintain the first guide part 216 in multiple different positions corresponding to bone shortening of 2, 3, 4, and 5 mm.

In FIG. 20, a holding assembly/ratchet mechanism 224 is shown acting between the first guide part 216 and guide part 210 to close the gap formed upon removal of an ulnar bone fragment. Through this ratchet mechanism, progressively increasing pressure application may be applied between the bone parts 130, 132 preparatory to insertion of fixation components.

Optionally, a larger holding assembly/ratchet mechanism 226 may be utilized in place of, or in addition to, the ratchet mechanism 224 to act directly between the bone parts 130, 132 to draw them against each other to close the gap created by the removal of the bone fragment.

A drill guide 228 may be fixedly attached to the guide part 216. The drill guide 228 has one or multiple guide bores 230, the lines of which are substantially perpendicular to the bone surfaces 126, 128 produced by removing the bone fragment. Fixation utilizing the drill guide 228 may be performed as described with earlier embodiments herein.

The foregoing disclosure of specific embodiments is intended to be illustrative of the broad concepts comprehended by the invention.

The invention claimed is:

1. A method of performing an osteotomy, the method comprising the steps of:
providing a guide assembly;
providing a base assembly;
fixedly mounting the base assembly to abut against an exposed surface of a bone to be cut;
connecting the guide assembly to the base assembly to thereby place the guide assembly in operative relationship to the bone so that the guide assembly defines first and second guide edges that are fixed in operative, non-parallel relationship to each other to each guide movement of a cutting tool;
guiding the cutting tool along each of the first and second non-parallel guide edges without moving the guide assembly relative to the bone to produce first and second cut lines in the bone that allow separation of a fragment of the bone from between first and second bone surfaces formed respectively at the first and second cut lines;

separating the bone fragment so that a gap with a first width is formed between the first and second bone surfaces; and changing the width of the gap to be less than the first width.

2. The method of performing an osteotomy according to claim 1 wherein the base assembly in conjunction with the guide assembly makes up a first subassembly, and with the base assembly fixedly mounted to the bone and the guide assembly connected to the base assembly, the first subassembly is in an operative state.

3. The method of performing an osteotomy according to claim 2 wherein the step of providing a guide assembly comprises providing a guide assembly comprising a body on which the first and second guide edges are defined with a permanently fixed first angular relationship with each other.

4. The method of performing an osteotomy according to claim 3 further comprising the step of providing first and second guide assemblies each comprising a body on which first and second guide edges are defined with a permanently fixed non-parallel angular relationship with each other with the permanently fixed angular relationship of the first and second guide edges on the first guide assembly being different than the permanently fixed angular relationship of the first and second guide edges on the second guide assembly, and the step of providing a guide assembly comprises selecting a guide assembly from between the first and second guide assemblies based upon a desired permanently fixed angular relationship between the first and second guide edges.

5. The method of performing an osteotomy according to claim 2 wherein the guide assembly is fully separable from the base assembly.

6. The method of performing an osteotomy according to claim 2 further comprising the steps of providing a positioning guide and placing the positioning guide against the bone to align the base assembly in a position desired for the base assembly relative to the bone with the first subassembly in the operative state.

7. The method of performing an osteotomy according to claim 6 wherein the positioning guide is fully separable from the base assembly.

8. The method of performing an osteotomy according to claim 7 wherein one of the positioning guide and base assembly has a post with an axis and the other of the positioning guide and base assembly has a receptacle for the post and the positioning guide and base assembly are engageable and separable by being translated relative to each other along the post axis by respectively directing the post into the receptacle and withdrawing the post from the receptacle, wherein the cut lines each resides in a plane and the axis is substantially parallel to each of the planes of the cut lines.

9. The method of performing an osteotomy according to claim 6 further comprising the steps of separating the positioning guide from the base assembly and thereafter connecting the guide assembly to the base assembly to define the first subassembly.

10. The method of performing an osteotomy according to claim 9 wherein the step of placing the first subassembly in the operative state comprises fixing the base assembly to the bone.

11. The method of performing an osteotomy according to claim 2 wherein one of the base assembly and guide assembly has a post with an axis and the other of the base assembly and guide assembly has a receptacle for the post and the base assembly and guide assembly are engageable and separable by being translated relative to each other along the post axis by respectively directing the post into the receptacle and withdrawing the post from the receptacle, wherein the cut lines each resides in a plane and the axis is substantially parallel to each of the planes of the cut lines.

12. The method of performing an osteotomy according to claim 1 further comprising the step of providing a base assembly that in conjunction with the guide assembly makes up a first subassembly, the first subassembly having different operative states wherein the guide assembly is in its operative relationship to the bone, wherein the first and second guide edges have a first angular relationship with the first subassembly in a first operative state and a second angular relationship that is different than the first angular relationship with the first subassembly in a second operative state, wherein there is a first guide part on the first subassembly that is: a) releasably maintained in a first position relative to the bone with the first subassembly in the first operative state; and b) movable from the first position into a second position in which the first guide part can be releasably maintained with the first subassembly in the second operative state.

13. The method of performing an osteotomy according to claim 12 wherein the first guide part pivots around an axis as it is moved between the first and second positions.

14. The method of performing an osteotomy according to claim 13 wherein the first guide part pivots relative to a second guide part on the first subassembly and there is a holding assembly that acts directly between the first and second guide parts that maintains the first and second guide parts in at least one relationship.

15. The method of performing an osteotomy according to claim 14 further comprising the steps of providing a guide assembly on the first guide part and by using the guide assembly controllably directing a fixation component through the first and second bone surfaces after the width of the gap is reduced to place first and second bone parts on which the first and second bone surfaces are respectively formed in a final desired relationship wherein the first and second surfaces are either against or adjacent to each other, the fixation component maintaining the first and second bone parts in the final desired relationship and preventing separation of the first and second bone surfaces.

16. The method of performing an osteotomy according to claim 12 wherein the first guide part is releasably maintained in the first and second positions through a ratchet mechanism.

17. The method of performing an osteotomy according to claim 1 wherein the step of changing the width of the gap comprises using a separate instrument to engage bone parts on opposite sides of the gap and produce forces on the bone parts that cause the first and second bone surfaces to be urged towards each other.

18. The method of performing an osteotomy according to claim 17 wherein the separate instrument has an associated ratchet mechanism through which different forces can be generated and maintained that cause the first and second bone surfaces to be urged towards each other.

19. The method of performing an osteotomy according to claim 1 further comprising the step of directing a fixation component through the first and second bone surfaces after the width of the gap is reduced to place first and second bone parts on which the first and second bone surfaces are respectively formed in a final desired relationship wherein the first and second surfaces are either against or adjacent to each other, the fixation component maintaining the first and second bone parts in the final desired relationship.

20. The method of performing an osteotomy according to claim 1 wherein the first and second surfaces are defined respectively on first and second bone parts and further comprising the step of providing a holding assembly that acts between the first and second bone parts to maintain the bone parts in a relationship wherein the first and second surfaces are either against or adjacent to each other.

21. The method of performing an osteotomy according to claim 20 wherein the holding assembly acts between the first and second bone parts so that the first and second bone surfaces are urged towards each other.

22. The method of performing an osteotomy according to claim 1 wherein the step of changing the width of the gap comprises using an instrument with first and second parts respectively on first and second bone parts on which the first and second bone surfaces are respectively formed in a manner so as to cause the first and second bone surfaces to be moved against or adjacent to each other, the first instrument part having a guide assembly, the method further comprising the step of using the guide assembly to controllably direct a fixation component through the first and second bone surfaces after the width of the gap is reduced to maintain the first and second bone surfaces against or adjacent to each other.

23. A method of performing an osteotomy, the method comprising the steps of:

providing a base assembly;

mounting the base assembly to a bone to be cut;

providing a guide assembly;

connecting the base assembly to the guide assembly, the base assembly and guide assembly together making up a first subassembly;

placing the guide assembly in operative relationship to a bone to be cut so that the guide assembly defines first and second guide edges that are in fixed relationship to each other to each guide movement of a cutting tool;

guiding the cutting tool along each of the first and second guide edges to produce first and second cut lines in the bone to facilitate separation of a fragment of the bone from between first and second bone surfaces formed respectively at the first and second cut lines;

separating the bone fragment so that a gap with a first width is formed between the first and second bone surfaces;

changing the width of the gap to be less than the first width; and directing a fixation component through the first and second bone surfaces using the first subassembly as a guide to thereby urge the first and second surfaces either against or adjacent to each other into a final desired relationship.

* * * * *

UNITED STATES PATENT AND TRADEMARK OFFICE
CERTIFICATE OF CORRECTION

PATENT NO. : 8,939,984 B2
APPLICATION NO. : 13/294648
DATED : January 27, 2015
INVENTOR(S) : Jeffrey E. Budoff It is certified that error appears in the above-identified patent and that said Letters Patent is hereby corrected as shown below:

On the title page delete item (73).

Signed and Sealed this
Twenty-third Day of June, 2015

Michelle K. Lee
*Director of the United States Patent and Trademark Office*